United States Patent [19]
Kitahara

[11] Patent Number: 4,776,943
[45] Date of Patent: * Oct. 11, 1988

[54] DEVICE FOR DETECTING AIR-FUEL RATIO OF MIXTURE OVER WIDE RANGE FROM BELOW TO ABOVE STOICHIOMETRIC RATIO

[75] Inventor: Tsuyoshi Kitahara, Ina, Japan

[73] Assignee: Nissan Motor Co., Ltd., Yokohama, Japan

[*] Notice: The portion of the term of this patent subsequent to Apr. 2, 2003 has been disclaimed.

[21] Appl. No.: 18,857

[22] Filed: Feb. 24, 1987

Related U.S. Application Data

[63] Continuation of Ser. No. 702,538, Feb. 19, 1985, abandoned.

[30] Foreign Application Priority Data

Feb. 20, 1984 [JP] Japan .................... 59-28752

[51] Int. Cl.[4] ............................................. G01N 27/58
[52] U.S. Cl. ...................... 204/427; 204/406; 204/412; 204/425; 204/426; 204/428; 204/429
[58] Field of Search ............... 204/1 T, 406, 412, 424, 204/425, 426, 427, 428, 429; 123/489; 60/276

[56] References Cited

U.S. PATENT DOCUMENTS

| | | | |
|---|---|---|---|
| 4,101,403 | 7/1978 | Kita et al. | 204/195 |
| 4,158,166 | 6/1979 | Isenberg | 204/427 X |
| 4,207,159 | 6/1980 | Kimura et al. | 204/195 |
| 4,224,113 | 9/1980 | Kimura et al. | 204/1 |
| 4,264,425 | 4/1981 | Kimura et al. | 204/429 X |
| 4,272,329 | 6/1981 | Hetrick et al. | 204/412 X |
| 4,272,331 | 6/1981 | Hetrick | 204/426 X |
| 4,282,080 | 8/1981 | Muller et al. | 204/428 X |
| 4,292,158 | 9/1981 | Mueller et al. | 204/426 |
| 4,294,679 | 10/1981 | Maurer et al. | 204/592 R |
| 4,298,573 | 11/1981 | Fujishiro | 204/425 X |
| 4,300,990 | 11/1981 | Maurer | 204/426 X |
| 4,306,957 | 12/1981 | Ishitani et al. | 204/412 |
| 4,334,510 | 6/1982 | Croset et al. | 123/440 |
| 4,334,974 | 6/1982 | Muller et al. | 204/425 X |
| 4,366,039 | 12/1982 | Uchida et al. | 204/406 |
| 4,384,935 | 5/1983 | De Jong | 204/426 X |
| 4,505,783 | 3/1985 | Mase et al. | 204/429 X |
| 4,505,802 | 3/1985 | Mase et al. | 204/427 X |
| 4,505,807 | 3/1985 | Mase et al. | 204/428 X |
| 4,578,172 | 3/1986 | Yamada et al. | 204/406 X |
| 4,580,539 | 4/1986 | Kitahara | 204/428 X |

FOREIGN PATENT DOCUMENTS

| | | |
|---|---|---|
| 1071709 | 2/1980 | Canada . |
| 57-76450 | 5/1982 | Japan . |
| 57-192850 | 11/1982 | Japan . |
| WO85/00658 | 2/1985 | PCT Int'l Appl. . |
| 2097541 | 11/1982 | United Kingdom . |

Primary Examiner—John F. Niebling
Assistant Examiner—Nam X. Nguyen
Attorney, Agent, or Firm—Foley & Lardner, Schwartz, Jeffery, Schwaab, Mack, Blumenthal & Evans

[57] ABSTRACT

A device detects an air-fuel ratio of a fuel mixture by causing an electric current to flow through an oxygen ion-conductive solid electrolyte to cause migration of oxygen ions between an atmospheric air and a gas receiving portion into which the exhaust gases resulting from combustion of the fuel mixture are diffused via gas diffusion restricting means. The device includes means for detecting the electric current.

23 Claims, 7 Drawing Sheets

DEVICE FOR DETECTING AIR-FUEL RATIO OF MIXTURE OVER WIDE RANGE FROM BELOW TO ABOVE STOICHIOMETRIC RATIO

This application is a continuation of application Ser. No. 702,538, filed Feb. 19, 1985, now abandoned.

BACKGROUND OF THE INVENTION

The present invention relates to a device for detecting an air-fuel ratio of an air-fuel mixture over a wide range from below the stoichiometric ratio (rich) for the mixture to above the stoichiometric ratio (lean) for the mixture by exposing a probe or a sensing element to exhaust gases resulting from combustion of the mixture.

In automobiles, it is necessary to detect an air-fuel ratio of a mixture supplied to an internal combustion engine for controlling the supply of fuel to the engine so as to adjust the actual air-fuel ratio to a target value. Common practice to detect the air-fuel ratio is to expose an oxygen sensing element, viz., an oxygen sensor, to exhaust gases discharged by the internal combustion engine and measure oxygen partial pressure in the exhaust gases.

Japanese patent application primary publication No. 57-76450 discloses a device for detecting an air-fuel ratio of an air-fuel mixture having an air-fuel ratio above the stoichiometric ratio for the mixture by measuring an oxygen partial pressure in exhaust gases resulting from the combustion of the mixture by exposing an oxygen sensing element to the exhaust gases. This known device is further described referring to FIG. 1. As illustrated in FIG. 1, the oxygen sensing element comprises an oxygen ion-conductive solid eletrolyte 1 having a measurement electrode layer 2 on one side thereof and a reference electrode layer 3 on the other side thereof. A DC voltage is applied between the electrode layers 2 and 3 to cause an electric current $I_s$ to flow through the solid electrolyte 1 from the electrode 3 to the electrode 2. For restricting inflow of oxygen to the measurement electrode 2, a porous coating layer 4 covers the electrode 2. Another coating layer 5 covers and protects the other electrode layer 3. The inflow of the electric current $I_s$ causes oxygen ions $O^{2-}$ to migrate from the electrode layer 2 to the electrode layer 3. As a result, a reference oxygen partial pressure Pa develops at the reference electrode layer 3 and an oxygen partial pressure Pb, viz., an oxygen partial pressure in the exhaust gases, develops at the measurement electrode 2. An electromotive force E produced by the sensing element may be expressed by Nernst's equation as follows:

$$E = (RT/4F) \ln(Pa/Pb) \qquad (1)$$

where: R is the gas constant, T the absolute temperature, and F the Faraday constant.

This electromotive force E may be measured and taken out in terms of an output Vs of the sensing element. The output Vs exibits different voltage versus λ characteristics for different magnitudes of the electric current $I_s$ as shown in FIG. 2 where λ=(actual air-fuel ratio)/(the stoichiometric ratio). As will be readily understood from FIG. 2, since, if the electric current $I_s$ is kept constant, the output Vs varies versus air-fuel ratio within a narrow range of λ, an actual air-fuel ratio within the narrow range can be detected by the sensor output Vs. This. however, is not practical for detection of air-fuel ratio over a wide range. To overcome this problem, it is proposed to keep the voltage Vs at a target value Va (see FIG. 2) and measure an electric current $I_s$ which is variable in proportion to variation in λ over a wide range as shown by a fully drawn curve in FIG. 3 as long as the air-fuel ratio is above the stoichiometric ratio (λ>1).

This known device, however, is not suitable for detecting an air-fuel ratio of a rich mixture (λ<1) because, as will be understood from FIG. 3, the current $I_s$ increases again as the mixture becomes rich as shown by a broken line curve. This characteristic exibited by the current $I_s$ when the air-fuel ratio is below the stoichiometric ratio is derived from the fact that an equilibrium state with the exhaust gases resulting from combustion of a rich air-fuel mixture is not accomplished so that oxygen ions within the solid electrolyte are only diffused into the ambient exhaust gas environment in the form of oxygen molecules because the content of oxygen in the exhaust gases is almost zero. This explains why the migration of oxygen ions increase and thus the electric current $I_s$ increases as the air-fuel ratio shifts to the rich side beyond the stoichiometric ratio.

As a result, with the same measured magnitude in the electric current $I_s$, a single air-fuel ratio cannot be identified because two air-fuel ratio values are present within a range near the stoichiometric ratio. Thus, it is impossible to identify the actual air-fuel ratio by relying on the measurement result of the electric current $I_s$ only. In other words, the use of this known device is confined to detecting an air-fuel ratio above the stoichiometric ratio. Besides, since both of the electrode layers 2 and 3 are exposed to the exhaust gases, the electrodes 2 and 3 are deteriorated at a fast rate. The solid electrolyte is deteriorated, too, when the sensing element is used for a long time to detect a rich air-fuel ratio because a material $ZrO_2$ which constitutes the solid electrolyte 1 is decomposed into ions, oxygen ions of which are diffused into the exhaust gases. Thus, the output characteristic of the sensing element ($I_s$ versus A/F characteristic) varies for a time (age) and the endurability is not satisfactory.

SUMMARY OF THE INVENTION

An object of the present invention is to provide a device, free from the above problems, for detecting an air-fuel ratio of a fuel mixture over a wide range from below the stoichiometric ratio (rich) to above the stoichiometric ratio (lean).

Another object of the present invention is to provide a device for detecting an air-fuel ratio which has a sufficiently long endurability such that it can sustain stable output characteristic for a long time even if it is used to probe exhaust gases resulting from combustion of a fuel-rich mixture.

One aspect of the present invention is to provide a device for detecting an air-fuel ratio of a fuel mixture by probing exhaust gases resulting from combustion of the fuel mixture, the exhaust gases including at least oxygen and combustion by-products, comprising:

a partition having a first side and a second side opposite to said first side, said partition defining on said first side an atmospheric air receiving portion communicating with the ambient atmosphere and on said second side a gas receiving portion communicating with a source of the exhaust gases;

said partition having at least a portion formed of an oxygen ion-conductive solid eletrolyte;

first electrode means exposed to said atmospheric air receiving portion;

second electrode means exposed to said gas receiving portion, said first and second electrode means interposing said electrolyte therebetween;

means for restricting gas diffusion of said exhaust gases to said gas receiving portion;

current providing means for providing an electric current to flow between said first and second electrode means through said electrolyte in such a manner as to cause migration of oxygen ions through said electrolyte between said atmospheric air receiving portion and said gas receiving portion so as to keep an oxygen partial pressure ratio across said electrolyte constant; and means for detecting said electric current.

Another aspect of the present invention is to provide a sensing element for probing exhaust gases resulting from combustion of a fuel mixture, comprising:

a partition having a first side and a second side opposite to said first side, said partition defining on said first side an atmospheric air receiving portion communicating with the ambient atmosphere and on said second side a gas receiving portion communicating with a source of the exhaust gases;

said partition having at least a portion formed of an oxygen ion-conductive solid eletrolyte;

first electrode means exposed to said atmospheric air receiving portion;

second electrode means exposed to said gas receiving portion, said first and second electrode means interposed said electrolyte therebetween; and means for restricting gas diffusion of said exhaust gases to said gas receiving portion.

Still another aspect of the present invention is to provide a method for detecting an air-fuel ratio of a fuel-rich mixture which is below the stoichiometric ratio for the mixture by probing exhaust gases resulting from combustion of the fuel-rich mixture, the exhaust gases including combustible by-products, said method comprising the steps of:

providing a sensing element comprising a partition having a first side and a second side opposite to said first side, said partition defining on said first side an atmospheric air receiving portion communicating with the ambient atmosphere and on said second side a gas receiving portion communicating with a source of the exhaust gases, said partition having at least a portion formed of an oxygen ion-conductive solid eletrolyte, first electrode means exposed to said atmospheric air receiving portion, second electrode means exposed to said gas receiving portion, said first and second electrode means interposing said electrolyte therebetween, and means for restricting gas diffusion of said exhaust gases to said gas receiving portion;

causing an electric current to flow between said first and second electrode means through said electrolyte in such a manner as to cause migration of oxygen ions through said electrolyte between said atmospheric air receiving portion and said gas receiving portion so as to keep an oxygen partial pressure ratio across said electrolyte constant; and detecting said electric current.

DETAILED DESCRIPTION OF THE INVENTION

Referring to FIGS. 4 to 12 of the accompanying drawings, the present invention is further described.

Figure 1:
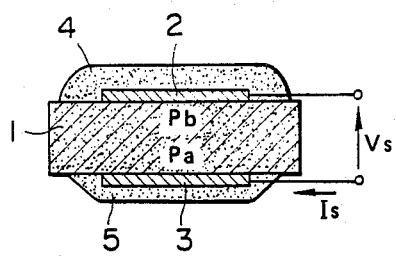
FIG. 1 is a cross sectional diagram showing a known oxygen sensing element discussed above.
Figure 2:
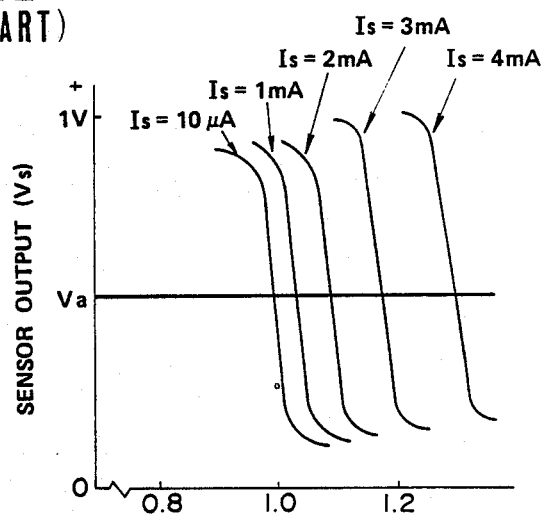
FIG. 2 is a graph showing the relationship between the output voltage and the air-fuel ratio.
Figure 3:
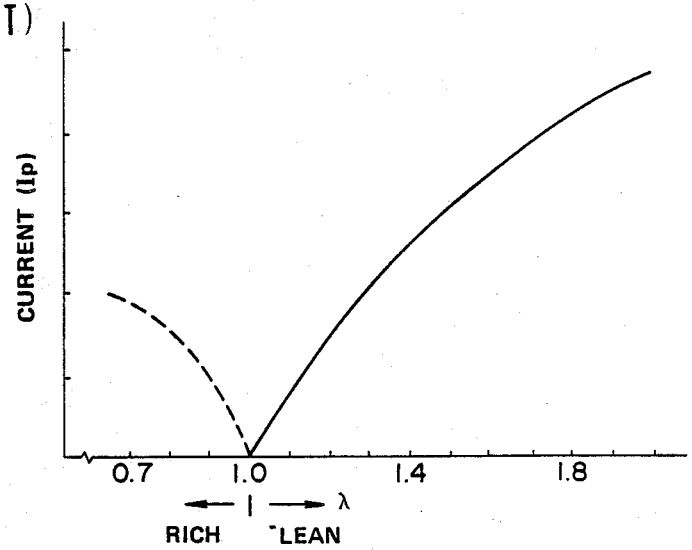
FIG. 3 is a graph showing the relationship between the inflow current and the airfuel ratio.
Figure 4:
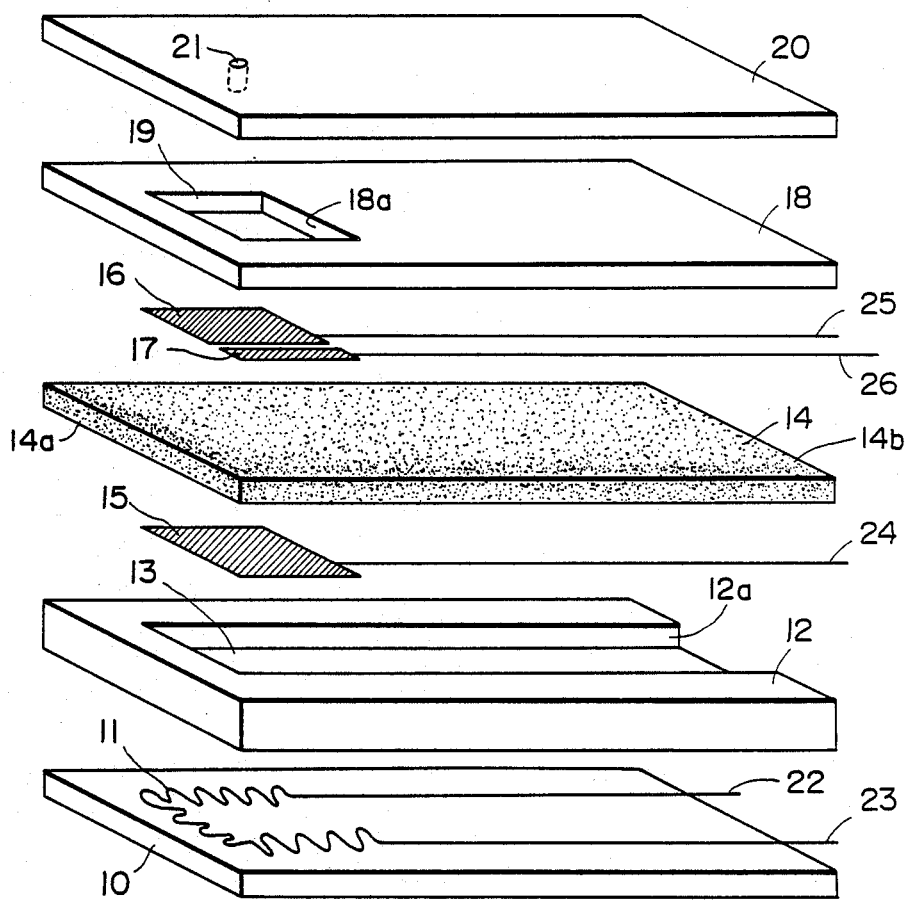
FIG. 4 is an exploded perspective view of a first embodiment of a sensing element according to the present invention.
Figure 5:
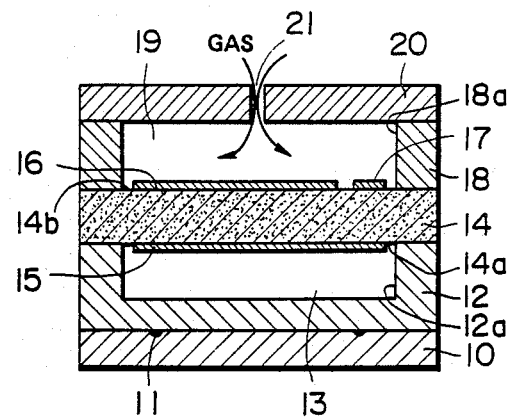
FIG. 5 is a cross sectional diagram of the sensing element.

Referring to FIGS. 4 and 5, a first embodiment of a sensing element (oxygen sensor) of a device for detecting an air-fuel ratio of a fuel mixture is illustrated. The sensing element comprises a partition 14 having a first side 14a and a second side 14b. The partition 14 defines on the first side 14a an atmospheric air receiving portion 13 communicating with the ambient atmosphere and on the second side 14b a gas receiving portion 19 communicating with a source of exhaust gases, such as an exhaust pipe of an automotive internal combustion engine, as best seen in FIG. 5. In this embodiment, the partition 14 is formed of an oxygen ion-conductive solid electrolyte. If desired, the partition 14 may be partly formed of the oxygen ion-conductive solid electrolyte such that that portion of the partition which is interposed between first electrode means 15 and second electrode means 16, 17 is formed of the oxygen ion-conductive solid electrolyte and the balance portion formed of another heat resistive material. The first electrode means includes a thin electrode layer 15 printed on the first side 14a of the partition 14 and exposed to the atmospheric air receiving portion 13, while the second electrode means includes a thin pump electrode layer 16 and a thin sensor electrode layer 17 which are arranged side by side.

Figure 6:
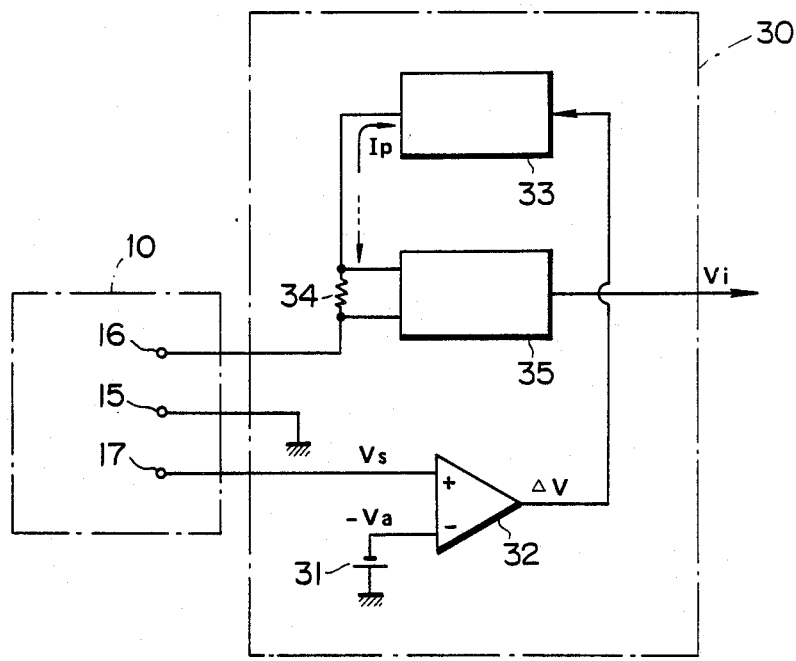
FIG. 6 is a block diagram of a device, according to the present invention, for detecting an air-fuel ratio using the sensing element shown in FIG. 4.

Referring to FIG. 4, there is shown a base plate 10 with an electrical heater 11 for heating the partition 14 of the oxygen ion-conductive solid electrolyte. Lying on the base plate 10 is an atmospheric air receiving plate 12 formed with a channel-like gutter 12a closed at one end. Lying on the atmospheric air receiving plate 12 is the partition 14 having printed on the first side thereof 14a the reference electrode layer 15 and on the opposite second side thereof 14b the pump and sensor electrode layers 16 and 17. The heater 11 has leads 22 and 23, and the electrode layers 15, 16 and 17 has leads 24, 25 and 26 connected as shown in FIG. 6. For restricting gas diffusion of the exhaust gases to the second electrode means 16 and 17, a plate 18 is laid on the second side 14b of the partition or solid electrolyte 14, which plate 18 is formed with a window-like opening 18a defining the side boundary of the gas receiving portion 19, and another plate 20 is laid on the plate 18, which plate 20 is formed with a small hole 21 for restricting gas flow communication between the gas receiving portion 19 and the ambient exhaust gas environment.

The base plate 10, atmospheric air receiving plate 12 and plates 18, 20 are formed of a heat resistive insulator, such as alumina and mullite or a heat resistive alloy. The solid electrolyte 14 is formed of a sintered body obtained by solidifying at least one selected from $C_2O$, $MgO$, $Y_2O_2$, $YB_2O_3$ into an oxide such as $ZrO_2$, $HrO_2$, $ThO_2$, $Bi_2O_3$.

Each of the electrodes 15, 16 and 17 includes platinum or gold as a main constituent thereof. The pump electrode 16 and the reference electrode 15 serve as electrodes which allows electric current to pass through the solid electrolyte 14 to cause the migration of oxygen ion within the solid electrolyte 14 so as to keep an oxygen partial pressure ratio, viz., a ratio between oxygen partial pressure at one side of the solid electrolyte and oxygen partial pressure at the other side thereof, constant. The sensor electrode 17 and the reference electrode 15 serve as electrodes for measuring an electric voltage developed across the solid electrolyte 14 due to the oxygen partial pressure ratio.

Referring to FIG. 6, the electrode layers 15, 16 and 17 are circuited with a detecting circuit 30. The circuit 30 comprises a source of electric voltage 31 which generates a target electric voltage $-Va$, a differential amplifier 32, a pump electric current supply unit 33, a resistor 34 and a pump electric current detecting unit 35 which detects the pump electric current by measuring the electric voltage across the resistor 34.

The differential amplifier 32 functions to compare a potential Vs of the reference electrode 15 of the sensing element relative to the sensor electrode 17 with the target electric voltage $-Va$, and calculate the difference therebetween $\Delta V$ ($\Delta V = Vs - (-Va)$). The pump electric voltage supply unit 33 regulates an outflow of the pump electric current Ip from the pump electrode 16 of the sensing element (or an inflow thereto) so as to reduce the output $\Delta V$ of the differential amplifier 32 toward zero. That is, when the output $\Delta V$ is positive, Ip is increased, whereas when the output $\Delta V$ is negative, Ip is decreased.

The pump electric current detecting unit 35 detects the pump electric current Ip by measuring a difference in electric potential across the resistor 34 in terms of the electric voltage Vi (Vi<Ip). The direction of flow of the pump electric current Ip as indicated by the fully drawn arrow in FIG. 6 is regarded as the positive direction and in this case the electric voltage Vi detected becomes positive, whereas when the direction of the pump electric current is negative as indicated by a broken arrow, the electric voltage Vi becomes negative.

The operation of this embodiment is described.

Although any value is set as the target electric voltage $-Va$ generated by the source of electric voltage 31 as long as it corresponds to a value which may be taken by the electric voltage Vs generated at the sensor electrode 17, it is preferable for the purpose of accurately converging the electric voltage Vs to the target value that the target electric voltage should take a value at which a tangent in variation in the electric voltage Vs versus variation in oxygen concentration within the gas receiving portion 19 is the largest, that is, a middle value between the upper and lower limits between which the electric voltage rapidly changes versus variation in the oxygen concentration.

If $-500$ mV is set as the target value $-Va$, the pump electric current supply unit or circuit 33 controls the supply of the pump electric current Ip in such a manner as to accomplish the relationship; $Vs = -500$ mV. Assuming that the temperature T is 1000° K., the oxygen partial pressures Pa and Pg within the atmospheric air receiving portion 13 of the sensing element and the gas receiving portion 19 thereof shall satisfy the following relationship which has been obtained by using the Nernst's equation;

$$Pg/Pa \approx 10^{-10}.$$

Substituting $Pa \approx 0.206$ atm, $Pg \approx 0.206 \times 10^{-10}$ atm.

Assuming the oxygen partial pressure within the exhasut gases is Px, the quantity Q of oxygen $O_2$ entering the gas receiving portion 19 past the small hole 21 can be expressed as $Q = D(Px - Pg)$, where D is the diffusion coefficient. Since $Pg = 0$, $$Q \approx D\, Px \qquad (1).$$

Since the quantity of oxygen ion $O^{2-}$ migrating within the solid electrolyte 14 is as high as this quantity Q, the following relation $Ip \propto Q$ holds. Thus, $$Ip = K_1 Px \qquad (2)$$

$K_1$: a constant.

Figure 7:
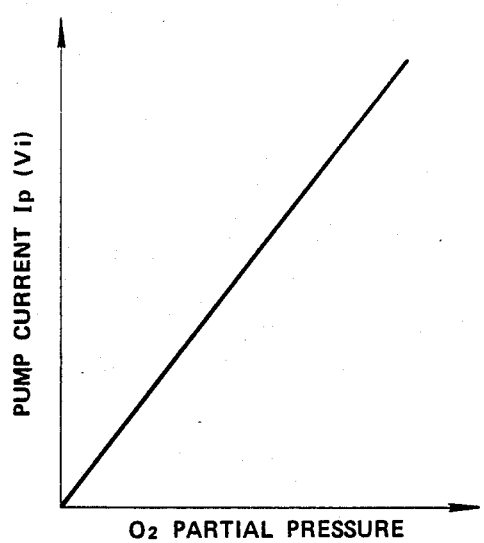
FIG. 7 is a graph showing the relationship between the pump current and the oxgen partial pressure within the exhaust gases.

The pump electric current Ip therefor varies in proportion to the oxygen partial pressure (oxygen concentration) within the exhaust gases as shown in FIG. 7.

Since the oxygen concentration is closely related to the air-fuel ratio when the air-fuel ratio (A/F) of the mixture fed to the internal combustion engine is on the lean side ($\lambda > 1$), it is apparent that the air-fuel ratio can be accurately detected with this circuit.

Since the oxygen partial pressure Px within the exhaust gases ranges from $10^{-20}$ to $10^{-25}$ (equilibrium oxygen partial pressure). When the air-fuel ratio is on the rich side ($\lambda < 1$), the relationship $Ip \approx 0$ should result from calculation using the equation (2).

However, when the air-fuel ratio is on the rich side, the exhaust gases contain much activate gases, HC and CO, for example. Taking CO as an example, the migration of oxygen ion in the opposite direction from the atmospheric air receiving portion 13 side to the gas receiving portion 19 side is needed so as to establish the relationship $Pg \approx 10^{-10} \times 0.206$ provided Px is between $10^{-20}$ and $10^{25}$.

However, the oxygen $O_2$ having migrated to the surface of the pump electrode 16 of the gas receiving portion 19 is consumed by the reaction as expressed by an equation as follows,

$$2CO + O_2 \rightarrow 2CO_2 \qquad (3).$$

Thus, when the air-fuel ratio is on the rich side, the rate of consumption of the oxygen $O_2$ by the reaction expressed by the equation (3) is measured in terms of the pump electric current Ip. In other words, what is measured is the rate of the reaction expressed by the above equation (3).

The rate of reaction expressed by the equation (3) is proportional to the amount of CO flowing into the gas receiving portion 19 past the small hole 21. Since the CO partial pressure within the gas receiving portion 19 is almost zero due to the consumption by the reaction expressed by the equation (3), the amount (Qco) of CO flowing into the gas receiving portion 19 past the small hole 21 is expressed by, $$Qco = D'(Pco - Pg)$$

where: Pco is the CO partial pressure within the exhaust gases and $D'$ the diffusion coefficient. Substituting $Pg \approx 0$, $$Qco = D'Pco.$$

Therefore, the amount of $O_2$ migrated by pumping from the atmospheric air receiving portion 13 by means of the pump electric current Ip is proportional to the amount of $O_2$ necessary to keep the oxygen partial pressure Pg within the gas receiving portion 19 at the value $0.206 \times 10^{-10}$. In other words, the pump current Ip is proportional to the concentration of CO within the exhaust gases.

When the air-fuel ratio is on the rich side, the concentration of CO (or CO+HC) is closely related to the air-fuel ratio, the air-fuel ratio can be accurately and continuously detected by measuring the pump current Ip even if the air-fuel ratio is on the rich side.

Figure 8:
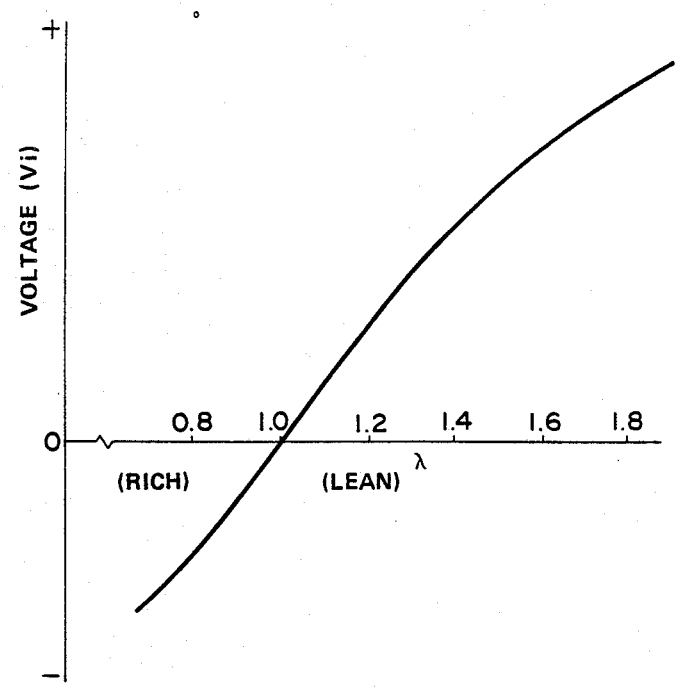
FIG. 8 is a graph showing the relationship between the measured voltage and the air-fuel ratio.

Thus, the electric voltage Vi that is proportional to the pump current Ip detected by the air-fuel detecting circuit 30 shown in FIG. 6 varies singularly and continuously with the variation in air-fuel ratio from the rich side to the lean side over the wide range as shown in FIG. 8.

In the case of the sensing element shown in FIGS. 4 and 5, since that side of the solid electrolyte 14 on which the reference electrode 15 lies is disposed within the atmospheric air receiving portion 13 and the opposite side of the solid electrolyte 14 where the pump and sensor electrodes 16 and 17 lie is disposed within the gas receiving portion 19 that communicates with the gas to be measured via the small hole 21, none of the electrodes 15 to 17 are exposed directly to the exhaust gases, thus reducing the rate at which the electrodes are deteriorated.

Since even when the air-fuel ratio is on the rich side and thus there is little oxygen left in the exhaust gases the oxygen partial pressure ratio across the solid electrolyte 14 is kept constant owing to the above mentioned migration of oxygen ion from the atmospheric air receiving portion 13 to the gas receiving portion 19, the decomposition of the material $ZrO_2$ of the solid eletrolyte 14 into ions does not occur, thus enhancing the endurability of the sensing element.

Figure 9:
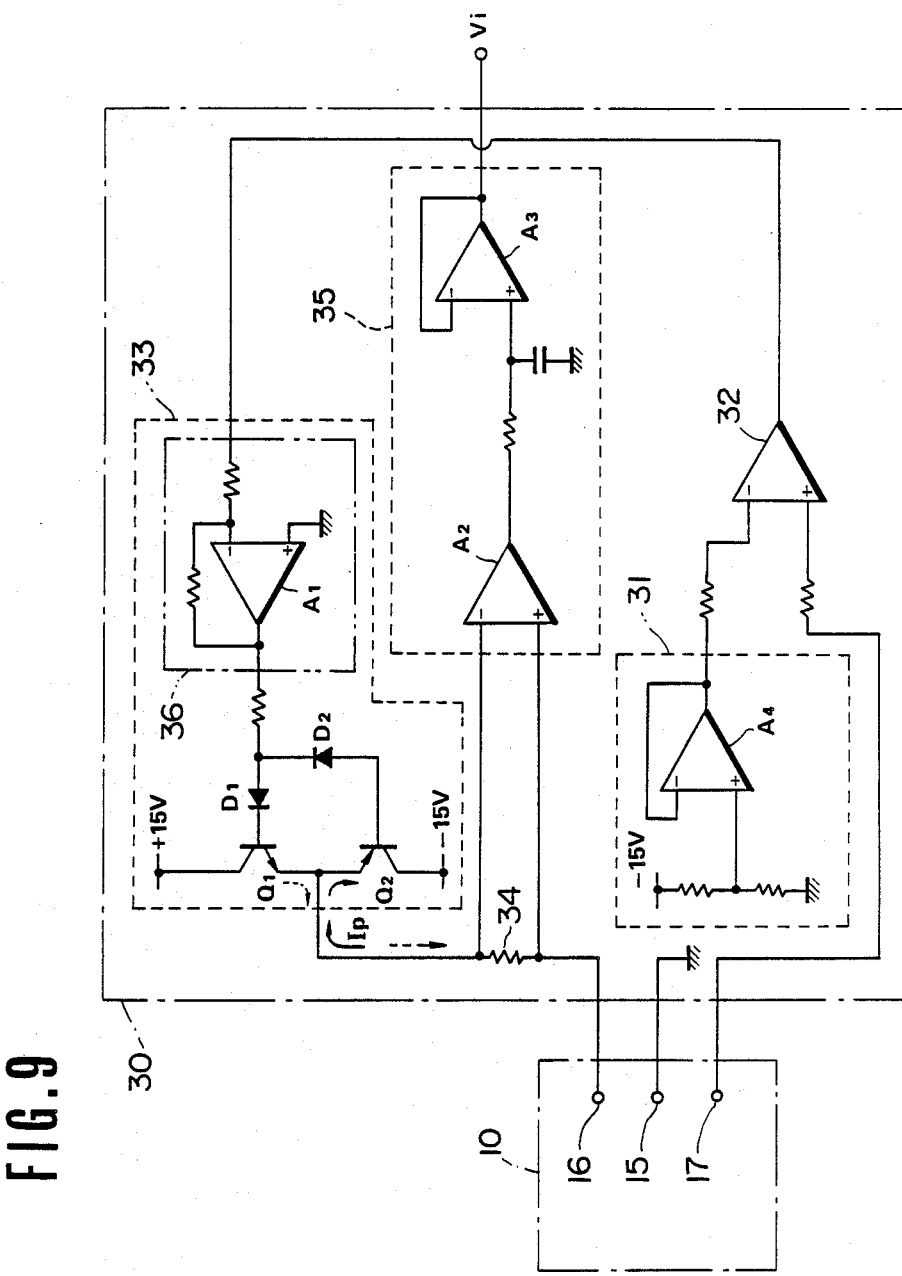
FIG. 9 is the detailed circuit diagram of the device shown in FIG. 6.

Referring to FIG. 9, the detecting circuit 30 is further described where the same reference numerals as used in FIG. 6 are used to designate counterparts. The reference character $A_1$ designates an operation amplifier, $A_2$ a differential amplifier, $A_3$ and $A_4$ buffer amplifiers, respectively.

The pump current supply unit 33 regulates the amount and the direction of the pump current Ip such that the difference indicative signal $\Delta V$ generated by the differential amplifier is fed to an inverter amplifier 36 including the operational amplifier $A_1$, and a complementary phase inverter circuit including transistors $Q_1$, $Q_2$ and diodes $D_1$, $D_2$ regulates the amount and the direction of the pump current Ip in response to the output of the inverter amplifier 36 so as to decrease $\Delta V$ to zero.

The pump electric current detecting unit 35 includes the differential amplifier $A_2$ which detects the difference in potential across the resistor 34 and thus detects Ip in terms of electric voltage Vi and generates the output of the differential amplifier $A_2$ via the buffer amplifier $A_3$.

Figure 10:
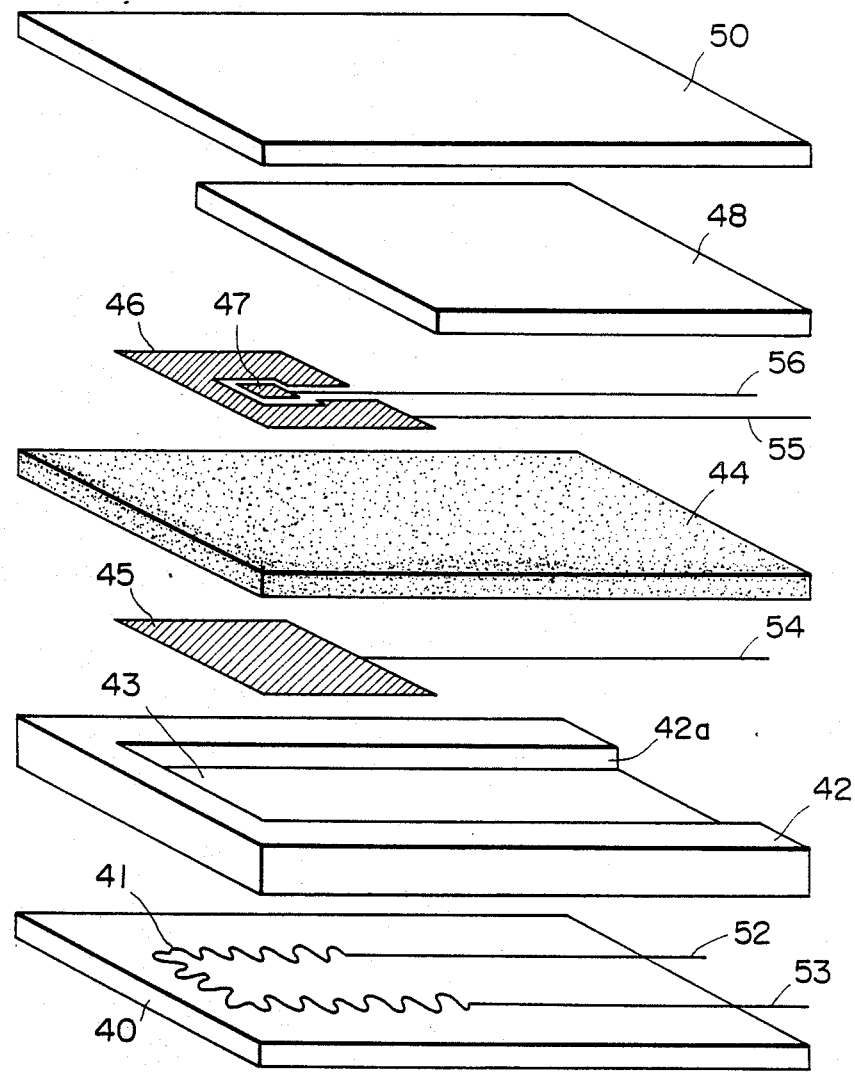
FIG. 10 is an exploded perspective view of a second embodiment of a sensing element according to the present invention.
Figure 11:
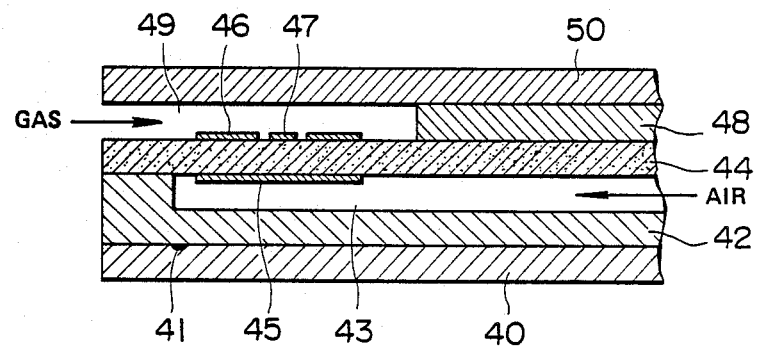
FIG. 11 is a longitudinal cross sectional diagram of the sensing element shown in FIG. 10.

Next, a second embodiment of a sensing element according to the present invention is described referring to FIGS. 10 and 11 which respectively show an exploded perspective view thereof and a longitudinal cross sectional view through the electrode mounting portion thereof.

This embodiment features that a clearance defined between two plates serves not only as a gas receiving portion but also as means for restricting diffusion of gas.

Referring to the structure of this embodiment, similarly to the first embodiment, there is a base plate 40 with a heater 41 and lying on the base plate is an atmospheric air receiving plate 42 formed with a channel-like gutter 42a defining an atmospheric air receiving portion 43. Lying on the atmospheric air receiving plate 42 is a partition of an oxygen ion-conductive solid electrolyte 44.

Similarly with the first embodiment, there is a rectangular thin electrode layer 45 formed on the solid eletrolyte 44. However, there is a difference in that a pump electrode layer 46 and a sensor electrode layer 47 which are to be arranged in opposed relationship with the reference electrode layer 45 are formed such that the pump electrode layer 46 is rectangular and has the sensor electrode layer 47 disposed in the center rectangular opening formed through the center portion thereof in such a manner as to surround the outer periphery of the latter.

A plate 50 is connected to the solid electrolyte with a spacer 48 interposed therebetween (the spacer may be replaced with an adheasive layer), leaving a distance (0.1 mm, for example), creating a clearance 49 between the electrode arranged portion of the solid electrolyte 44 and the plate 50, causing this clearance 49 to serve as means for restricting diffusion of gas.

Designated by 52, 53 in FIG. 10 are leads for the heater 41, designated by 54 to 56 are leads for the reference electrode 45, pump electrode 46 and sensor electrode 47, respectively. The materials of the component parts of this embodiment are similar to the first embodiment.

Similarly to the first embodiment, the air-fuel ratio of the mixture fed to the internal combustion engine can be continuously and accurately detected over the wide range from the rich side to the lean side by means of a detecting circuit similar to that shown in FIG. 6, and besides the endurability is enhanced similarly to the first embodiment.

Since the diffusion of gas is restricted by the clearance which is open to the environment filled with gas to be measured at a plurality of sides thereof (three sides in this example), there occurs little influence on the diffusion restricting performance owing to the deposit of the components of the exhaust gases, thus ensuring stable operation over a prolonged time. The distance and shape formed by the clearance may be easily varied as desired by varying the thickness of the spacer 48, thus making the design change and quality control easy.

Figure 12:
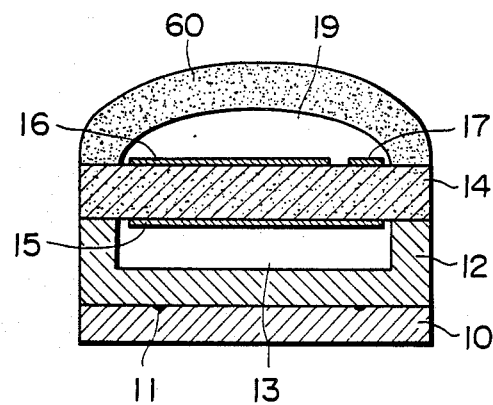
FIG. 12 is a similar cross sectional diagram to FIG. 5 showing a third embodiment of a sensing element according to the present invention.

FIG. 12, which is a similar view to FIG. 5, illustrates a third embodiment resulting from a slight modification of the first embodiment according to the present invention. In FIG. 12, the same reference numerals as used in FIG. 5 are used to designate counterparts, and their description is omitted.

The third embodiment is different from the first embodiment in that a gas receiving portion 19 is covered by a porous sintered body 60 and this sintered body 60 is used to serve as means for restricting diffusion of gas. Similar effects as in the case of the first embodiment are provided with this third embodiment.

It is more practical for ease in manufacturing to fill the space serving as the gas receiving portion 19 with the porous material because the porous material ensures the inflow of gas.

Although, in each of the above described embodiments, the common reference electrode is placed on the partition of the solid electrolyte at its atmospheric air receiving side surface and the pump electrode and sensor electrode are separately placed on the partition at its gas receiving side surface, this relationship may be reversed. Alternatively, the reference electrodes may be separately provided for the pump and sensor electrodes, respectively.

If desired, the pump electrode and the sensor electrode may be formed as a common electrode so that this common electrode serves as an electrode for supplying the pump current and also as an electrode for measuring an electric voltage generated due to the oxygen partial pressures.

However, with this arrangement, what is measured as an electric voltage between the electrodes includes not only an electric voltage due to oxygen partial pressures but also a drop in electric voltage due to the internal resistance within the sensing element so that a compensation for this internal resistance is necessary in order for accurate setting of the target value which greatly effects the accuracy in keeping the oxygen partial pressure ratio across the solid electrolyte constant. For the compensation, as taught by laid-open Japanese patent application publication No. 57-192850, an AC current is superimposed on the inflowing current between the electrodes of the sensing element, and a DC current portion of the signal measured across the resistor 34 shown in FIG. 6 is used as the detected signal Ip and an AC current portion of the signal is used to calculate the internal resistance. The AC current portion is multipled with the signal Ip detected by measuring the DC current portion to provide a voltage drop and a value including this voltage drop is set as the target electric voltage value. With this target value, the air-fuel ratio can be accurately detected over the wide range similarly to the preceding embodiments.

As will now be understood from the preceding description, the air-fuel ratio of the mixture fed to the internal combustion engine can be singularly and accurately detected over the wide range by the use of the sensing element according to the present invention by supplying the pump current (the forward and reverse directions of the current available) to the solid electrolye so as to keep the oxygen partial pressure ratio across the solid electrolyte constant and then measuring the pump current.

Besides, with the sensing element according to the present invention, the deterioration of the electrodes is extremely reduced, the output characteristic is stable and sufficiently long endurability is provided because the solid electrolyte and the electrodes thereon are not directly exposed to the exhaust gases and the decomposition of the solid electrolyte into ions does not occur even when the sensing element is used to probe the exhaust gases resulting from combustion of a fuel-rich mixture.

I claim:

1. A device for detecting an air-fuel ratio of a fuel mixture by probing exhaust gases resulting from combustion of the fuel mixture, the exhaust gases including at least oxygen and combustion by-products, comprising:

a partition having a first side and a second side opposite to said first side, said partition defining on said first side an atmospheric air receiving portion communicating with the ambient atmosphere and on said second side a gas receiving portion communicating with the exhaust gases;

said partition having at least a portion formed of an oxygen ion-conductive solid electrolyte;

first electrode means exposed to said atmospheric receiving portion;

second electrode means exposed to said gas receiving portion, said first and second electrode means interposing therebetween said portion formed of said oxygen ion-conductive solid electrolyte;

means for restricting gas diffusion of the exhaust gases to said gas receiving portion;

means, including third electrode means disposed on said portion of said partition and exposed to said gas receiving portion, for applying a predetermined electric voltage across said portion, formed of said ion-conductive solid electrolyte, causing DC electric current to flow between said first and third electrode means through said portion formed of said ion-conductive solid electrolyte;

means for comparing an actual voltage between said first electrode means and said second electrode means with a target voltage to give a difference therebetween and generating a difference indicative signal;

means responsive to said difference indicative signal for controlling the polarity and intensity of said DC electric current in such a manner as to decrease said difference indicative signal toward zero; and means for measuring said DC electric current and generating an output signal indicative of said DC electric current measured.

2. A device as claimed in claim 1, wherein said gas diffusion restricting means includes:

a first plate lying on said second side of said partition, said first plate being formed with an opening; and a second plate lying on said first plate to close said opening, said partition, said first plate and said second plate cooperating with each other to define said gas receiving portion within said opening, said second plate being formed with a gas flow restricting hole for providing restricted flow communication between said gas receiving portion and the source of the exhaust gases.

3. A device as claimed in claim 1, wherein said gas diffusion restricting means includes:

a plate lying on said second side of said partition and having a portion spaced distant from said second side of said partition to define a clearance therebetween, said plate and said partition cooperating with each other to define said gas receiving portion within said clearance.

4. A device as claimed in claim 1, wherein said gas diffusion restricting means includes:

a porous sintered body on said second side of said partition to cooperate with said partition to define said gas receiving portion.

5. A device as claimed in claim 1, wherein said gas diffusion restricting means includes:

a porous sintered body on said second side of said partition and formed with a recess, said porous sintered body and said partition cooperating with each other to form said gas receiving portion within said recess.

6. A device as claimed in claim 1, wherein said first electrode means includes an electrode layer printed on said electrolyte.

7. A device as claimed in claim 6, wherein said electrode layer of said first electrode means is grounded.

8. A device as claimed in claim 1, wherein said second electrode means includes a pump electrode layer printed on said electrolyte and a sensor electrode layer printed on said electrolyte.

9. A device as claimed in claim 8, wherein said pump electrode layer and said second electrode layer are arranged side by side.

10. A device as claimed in claim 8, wherein said pump electrode layer is formed with an opening and said sensor electrode layer is arranged within said opening.

11. A device as claimed in claim 1, further comprising a plate lying on said first side of said partition and formed with a gutter closed at one end, said plate cooperating with said first side of said partition to define said atmospheric receiving portion within said gutter.

12. A device as claimed in claim 1, further comprising electrical heating means for heating said electrolyte.

13. A sensing element for probing exhaust gases resulting from combustion of a fuel mixture, comprising:

a partition having a first side and a second side opposite to said first side, said partition being formed of an oxygen ion-conductive solid electrolyte;

an atmospheric air receiving plate, formed of an insulator, lying on said first side of said partition and formed with a longitudinal gutter closed at one end which defines an atmospheric air receiving portion on said first side of said partition, said longitudinal gutter being open at the opposite end to allow communication with ambient atmosphere;

a base plate, formed on an insulator, lying on said ambient air receiving plate;

a heater positioned between said atmospheric air receiving plate and said base plate and in direct contact with said air receiving plate;

means cooperating with said partition for defining a gas receiving portion on said second side of said partition and in communication with the exhaust gases;

first electrode means disposed on said first side of said partition and exposed to said atmospheric air receiving portion;

second electrode means, and third electrode means disposed on said second side of said partition and exposed to said gas receiving portion; and means for restricting gas diffusion of the exhaust gases to said gas receiving portion.

14. A sensing element as claimed in claim 13, wherein said gas receiving portion defining means includes:

a first plate, formed of an insulator, lying on said second side of said partition, said first plate being formed with an opening surrounding said second electrode means; and said gas diffusion restricting means includes:

a second plate, formed of an insulator, lying on said first plate to close said opening, said second plate being formed with a gas flow restricting hole dimensioned to provide restricted flow communication.

15. A sensing element as claimed in claim 13, wherein said gas diffusion restricting means includes:

a plate lying on said second side of said partition and having a portion spaced distant from said second side of said partition to define a clearance therebetween, said plate and said partition cooperating with each other to define said gas receiving portion within said clearance.

16. A sensing element as claimed in claim 13, wherein said gas diffusion restricting means includes:

a porous sintered body on said second side of said partition to cooperate with said partition to define said gas receiving portion.

17. A sensing element as claimed in claim 13, wherein said gas diffusion restricting means includes:

a porous sintered body on said second side of said partition and formed with a recess, said porous sintered body and said partition cooperating with each other to form said gas receiving portion within said recess.

18. A sensing element as claimed in claim 13, wherein said first electrode means includes an electrode layer printed on said electrolyte.

19. A sensing element as claimed in claim 13, wherein said second electrode means includes a pump electrode layer printed on said electrolyte and a sensor electrode layer printed on said electrolyte.

20. A sensing element as claimed in claim 19, wherein said pump electrode layer and said sensor electrode layer are arranged side by side.

21. A sensing element as claimed in claim 19, wherein said pump electrode layer is formed with an opening and said sensor electrode layer is arranged within said opening.

22. A sensing element as claimed in claim 13, further comprising a plate lying on said first side of said partition and formed with a gutter closed at one end, said plate cooperating with said first side of said partition to define said atmospheric receiving portion with said gutter.

23. A sensing element as claimed in claim 13, further comprising electrical heating means for heating said electrolyte.

* * * * *